United States Patent [19]

Zey et al.

[11] Patent Number: 5,399,760

[45] Date of Patent: * Mar. 21, 1995

[54] COLOR CONTROL & STABILITY IN ACETAMINOPHEN

[75] Inventors: Edward G. Zey; Olan S. Fruchey; Thomas H. Shockley; Joe S. Trevino; B. Frank Wood, all of Corpus Christi; Daniel D. Lindley, Portland, all of Tex.

[73] Assignee: Hoechst Celanese Corporation, Somerville, N.J.

[*] Notice: The portion of the term of this patent subsequent to Sep. 6, 2011 has been disclaimed.

[21] Appl. No.: 105,724

[22] Filed: Aug. 11, 1993

Related U.S. Application Data

[63] Continuation-in-part of Ser. No. 54,731, Apr. 29, 1993, abandoned.

[51] Int. Cl.[6] ........................................... C07C 233/05
[52] U.S. Cl. .................................... 564/216; 564/142; 564/144; 564/223; 564/2
[58] Field of Search ................... 564/216, 223, 2, 259, 564/144

[56] References Cited

U.S. PATENT DOCUMENTS

| | | | |
|---|---|---|---|
| 3,113,150 | 12/1963 | Young | 564/216 |
| 3,748,358 | 7/1973 | Baron | 564/216 |
| 4,524,217 | 6/1985 | Davenport et al. | 564/223 |
| 4,607,125 | 8/1986 | Mott | 568/319 |
| 5,155,269 | 10/1992 | Dunn et al. | 564/144 |

FOREIGN PATENT DOCUMENTS

2672212 8/1992 France .

OTHER PUBLICATIONS

Merck Index, 10th Edition, 5135, p. 761, 1983.

Primary Examiner—Shailendra Kumar
Attorney, Agent, or Firm—James J. Mullen; Donald R. Cassady

[57] ABSTRACT

A method is provided for purifying crude N-acetyl-para-aminophenol (APAP) containing color bodies or their precursors, the method comprising: a) forming a solution of the crude APAP; and b) subsequently contacting the solution with substoichiometric quantifies of an acetylating agent for a sufficient period of time to convert said color bodies or their precursors to substantially non-color bodies/stable, colorless substances; said quantities of acetylating agent provided is such that substantially none of the APAP is converted to other compounds.

25 Claims, No Drawings

COLOR CONTROL & STABILITY IN ACETAMINOPHEN

RELATED APPLICATIONS

The present patent application is a continuation-in-part of patent application Ser. No. 08/054,731, filed Apr. 29, 1993, now abandoned.

BACKGROUND OF THE INVENTION

1. Field of the Invention

This invention relates to an improved method for the purification of N-acetyl-para-aminophenol (APAP), also known as acetaminophen. APAP is a well-known over-the-counter analgesic and anti-pyretic agent.

2. Description of Related Art

The following prior art references are disclosed in accordance with the terms of 37 CFR 1.56, 1.97, and 1.98.

U.S. Pat. No. 3,042,719, issued Jul. 3, 1962, to Hahn et al., discloses the purification of crude discolored APAP by acidifying an aqueous solution of the APAP with a mineral acid, filtering the solution while hot, and cooling the filtrate while adding an alkaline reducing sulfite, e.g., sodium hydrosulfite (sodium dithionite). A "decolorizing" carbon may be added to the hot solution.

U.S. Pat. No. 3,113,150, issued Dec. 3, 1963, to Young, teaches the preparation of "pure" APAP by reacting acetic anhydride with a mixture of p-aminophenol and water, cooling the reaction mixture to precipitate the APAP, filtering to remove excess acetic acid, neutralizing the wet APAP with ammonium hydroxide, and agitating the resulting solution with carbon black.

U.S. Pat. No.3,748,358, issued Jul. 24, 1973, to Baron, discloses the purification of APAP by treating it in aqueous solution with carbon which has been preliminarily treated with an acidic solution.

U.S. Pat. No. 3,781,354, issued Dec. 25, 1973, to Kosak, teaches the purification of APAP by treating it in hot aqueous solution with ferric chloride and adsorbing the colored by-product on activated carbon.

U.S. Pat. No. 4,524,217, issued Jun. 18, 1985, to Davenport et al., teaches an integrated process for the production of APAP comprising acetylating phenol by a Friedel-Crafts reaction, or subjecting phenyl acetate to a Fries rearrangement to produce 4-hydroxyacetophenone (4-HAP), reacting the 4-HAP with hydroxylamine or a hydroxylamine salt to form 4-HAP oxime, and subjecting the latter oxime to a Beckmann rearrangement to form APAP.

All of the aforementioned U.S. patents are incorporated herein by reference, including the entire disclosures thereof.

ADDITIONAL BACKGROUND INFORMATION

In the manufacture of APAP by any of the known methods, it has been found that there is a tendency for color bodies and color body precursors to form which cause the crude product to have or to develop subsequently an undesirable colored appearance. Because of this, various methods have been developed for the purification of APAP, which remove color bodies in addition to other impurities, such that the purified product has a substantially pure white appearance. These methods often include the addition to a hot aqueous solution of APAP containing color bodies of an adsorbent carbon, which is a well-known decolorizing agent. Some of these methods are described in the disclosures of several of the previously cited references.

It has been found that a disadvantage of decolorizing APAP by contacting a hot aqueous solution of the crude APAP with an adsorbent carbon is that certain impurities appear for the first time or increase as a result of such treatment, which impurities were not present previously, i.e., in the crude APAP before purification. In view of the fact that the main use for APAP is as a pharmaceutical, the presence of these impurities must be kept to a very low practical maximum, either by preventing their formation, or removing the bulk of them subsequent to the carbon treatment, or converting these impurities to substantially non-color bodies.

SUMMARY OF THE INVENTION

In accordance with this invention, a crude APAP containing undesirable color bodies or their precursors is subjected to a purification treatment comprising the steps of forming an aqueous or organic solution (or mixture) of the crude APAP, and subsequently contacting said solution with substoichiometric quantities of an acetylating agent for a sufficient period of time to cause said undesirable color bodies to be converted to non-color bodies or non-color-causing bodies; the quantities of acetylating agent are such that substantially none of the APAP is converted to other compounds. It has been found that the treatment of the aqueous solution of the crude APAP with the acetylating agent substantially reduces the undesirable color bodies (impurities) which are observed to form during the preparation of the crude APAP.

DESCRIPTION OF THE PREFERRED EMBODIMENTS

An aqueous solution of APAP containing color bodies which is subjected to the acetylating agent treatment will, in most cases, contain at least about four (4) weight percent of APAP and the solution will be at least hot enough to dissolve the APAP substantially completely, e.g., at least about 40° C., preferably from about 60° C. to about 130° C. The method of the invention is useful in the preparation of a relatively pure decolorized APAP, regardless of the manufacturing process used to produce the APAP since such method accomplishes the reduction of impurities or undesirable color bodies formed during preparation of the APAP. Thus, the APAP may be produced, for example, by the process illustrated in the examples of previously cited U.S. Pat. No. 4,524,217 as summarized in the foregoing description of the disclosure of that patent, or by the previously developed process of reacting paraaminophenol (PAP) with acetic anhydride, as described, for example, in previously cited U.S. Pat. No. 3,113,150.

As previously mentioned in the production of APAP by the herein-described prior art processes, undesirable color bodies or impurities are produced. One of the major impurity components relative to this color stability problem is paraaminophenol (PAP). We have discovered that the addition of small quantities, i.e. substoichiometric quantities, of an acetylating agent during the APAP crystallization step substantially reduces the PAP levels and thus provides a more color-stable product as measured by a total color index (TCI).

Once the crude APAP is produced by one or more of the prior art processes as described herein, the material is placed in a separate vessel where it can be dissolved in water. The crude APAP in hot aqueous solution can be treated with carbon such as activated carbon, if one so desires to pre-treat. After mixing the APAP and carbon, the carbon is filtered off and the resultant hot aqueous solution of crude APAP is placed in a separate vessel designated as a crystallizer where cooling takes place in order to form APAP crystals. It is desirable at this point that the aqueous solution containing the crude APAP be sufficiently hot in order that all of the crude APAP is dissolved therein.

Preferably, the temperature of the aqueous solution of crude APAP is at least 40° C., or more preferably from about 60° C. to about 130° C. At this point in the crystallizer, cooling is initiated and then a sufficient quantity of an acetylating agent is added to the hot aqueous solution of crude APAP and the resultant mixture is agitated for a period of time to insure that the undesirable color bodies (impurities), such as PAP, or possible derivatives therefrom, are converted to non-offensive materials, i.e., those which do not promote an adverse or undesired color.

The acetylating agent is basically any material which can convert PAP, or possible organic derivatives therefrom, or other organic amines, to APAP or any other chemical which is stable to oxidation and/or polymerization and which will not result in color contamination or adverse color promotion thereof. While it is not desired to be limited by any theory of the invention, it may be postulated that the acetylating agent functions to "tie up" aromatic amines and related color body precursors, and thereby reduce color stability problems. Acetylating agents which fall within this category, and thus can be employed in this invention include (but are not limited to) acetic anhydride, acetic-propionic anhydride, acetyl chloride, phenyl acetate, ketene, and mixtures thereof. It is to be understood that the term "acetylating agent" includes acylation agents such as propionic anhydride, methyl ketene, phenyl propionate, acetic-formic anhydride, and mixtures thereof.

The amount of acetylating agent used in this purification process is critical because of the possible conversion of the APAP to other compounds such as 4-acetoxyacetanilide (4-AAA). The acetylating agent is thus used in substoichiometric quantities, generally less than 2.0% by weight, based on the total weight of the crude APAP present. Preferably, the amount is from about 0.001% to about 1.5% by weight. It is also within the scope of this invention to use greater than 2.0%, e.g. 2.0 to 5.0%, if one so desires and if such greater amounts have little or no effect on the desired end product (APAP).

In another facet of the present invention, there is provided a process step for controlling the formation of 4-AAA which in large quantities, i.e. >400 ppm, can result in morphological changes in the APAP crystal structure which is undesirable. It is well known in the art that the acetylation of APAP will result in the production of 4-AAA; note International Journal of Pharmaceutics, 24 (1985) 239-258 which is incorporated herein by reference in its entirety.

In this facet of the present invention, it is desirable to control the formation of 4-AAA, in addition to reducing the color bodies. It has unexpectedly been found that such control can be effectuated by the controlled addition of the acetylating agent to the aqueous solution of crude APAP during the crystallization thereof. In this step, and after all the crude APAP has been dissolved in water at elevated temperatures, the solution is cooled to a temperature just above the freezing point of the solution, e.g. about −2° C. and during this cooling cycle, the acetylating agent is contacted with the aqueous solution. It has been found that this contacting can be conducted under three (3) different scenarios. First, the acetylating agent can be contacted with the APAP solution at one time interval by a single addition. Secondly, the acetylating agent can be contacted with the APAP solution at two (2) different temperature ranges by two (2) different additions thereof. Under these latter conditions, from about 25% to about 50% by weight of said acetylating agent is added to the APAP solution which is at a temperature of from about 80° C. to about 110°, and then the remainder of said agent, i.e. from about 50% to about 75% by weight, is added to the APAP solution which is at a temperature of from about 50° C. to about 70° C. It is also within the scope of this second step that the acetylating agent can be added in three (3) or more staged additions and at different temperature levels during the cooling cycle. In the third case, the acetylating agent is contacted with APAP solution during the cooling cycle (crystallization) by the continuous addition thereof.

In the above described three (3) process steps, which are independent of each other, the mechanism and/or theory of why the 4-AAA is controlled and the PAP content is lowest, is not clearly understood. However, this was quite unexpected when tested.

The following examples further illustrate the invention.

EXAMPLES 1–4

Runs With & Without Acetic Anhydride Addition

A series of four (4) runs were made in a small pilot plant type of operation using 3-gallon vessels. The first two runs were without the use of acetic anhydride. The second two runs used acetic anhydride as a color control agent during the crystallization step.

In each of the runs described herein, approximately 1300 grams of crude APAP in 4700 grams of water were charged into a vessel. Acetic anhydride (0 or 15.7 grams) was added to this mixture, and the resultant mixture was heated to 100° C. After remaining at this temperature for approximately ten (10) minutes, the vessel was cooled to 15° C. over the next three (3) hours, during which time APAP crystallized out of the solution. At the end of this time, the remaining APAP had been crystallized out of the solution. The solid APAP is removed from the solution by means of a centrifuge and dried.

The final APAP products obtained from these runs gave excellent color results as shown below:

|  | Run 1 W/O $Ac_2O$ | Run 2 W/O $Ac_2O$ | Run 3 W/ $Ac_2O$ | Run 4 W/ $Ac_2O$ |
| --- | --- | --- | --- | --- |
| Initial Color (IC) | 0.007 | 0.006 | 0.020 | 0.012 |
| Total Color Index (TCI)* | 0.065 | 0.064 | 0.047 | 0.032 |
| PAP, ppm | 18 | 21 | 8 | 8 |
| 4-AAA, ppm | — | — | 207 | 185 |
| Total Organic Impurity, ppm | 200 | 203 | 428 | 412 |

*Using a Shimadzu UV-160 UV-VIS spectrophotometer.

The data above indicates that the PAP levels are reduced in the final product with the acetic anhydride addition. Also, the TCI test of the product involving acetic anhydride treatment indicated a lower value of 0.032 and 0.047. The runs without acetic anhydride produced a typical TCI value of 0.064 and 0.065 for the operation.

The initial IC's of the runs without acetic anhydride are low (0,006 to 0,007). The IC values for the runs with acetic anhydride are at a slightly higher range (0.012 to 0,020) due to minor operational variances.

The impurity component (4-AAA) 4-acetoxyacetanilide was not detected in the runs without acetic anhydride, but in the runs with acetic anhydride, the range was at a high level (185 to 207 ppm). This occurred when using 15.7 gms of acetic anhydride in the crystallization step. This 4-AAA impurity increased the total organic impurity levels to about the 420 ppm level, which is acceptable.

EXAMPLES 5–13

Statistical Process Control (SPC) Runs Using 2 Gms Acetic Anhydride in the Crystallization Step Subsequent to the work above involving 15.7 gms acetic anhydride added prior to dissolution and recrystallization, nine (9) repeat runs were made using the addition of 2 gms acetic anhydride (0.13% of the crude APAP charged) in each run. The reasons for these SPC runs were to further evaluate the quality and color stability of the APAP product after introducing only 2.0 gms of acetic anhydride in the purification process and to produce a product containing <100 ppm 4-AAA. Overall, the final APAP products obtained from these repeat runs were of good quality and also maintained good color stability as measured by TCI. The results are shown below:

|  | Range | Average for Nine (9) Runs |
|---|---|---|
| Initial Color (IC) | 0.005–0.011 | 0.008 |
| Total Color Index (TCI) | 0.026–0.052 | 0.038 |
| PAP, ppm | 7–16 | 10 |
| 4-AAA, ppm | 32–58 | 42 |
| Total Organic Impurity, ppm | 117–183 | 143 |

The IC's of these nine (9) runs ranged between 0.005 and 0.011, which are acceptable. The TCI's ranged from 0.026 to 0.052 with an average of 0.038 which is approximately one-half of that observed in the case where no acetic anhydride was used. These results indicate an enhanced color-stable APAP product.

The PAP levels were also at a low range from 7 to 16 ppm with an average of 10 ppm. The new component (4-AAA) 4-acetoxyacetanilide levels were from 32 to 58 ppm, with an average of 42 ppm. These 4-AAA levels are acceptable.

Total organic impurities were satisfactory. They ranged between 117 to 183 ppm, with an average of 143 ppm, which is below industry specification limits.

Overall, these results indicate that a high quality APAP product can be produced with regard to using two (2) grams acetic anhydride. This treatment increases the 4-AAA component slightly but decreases the PAP and TCI levels significantly in the final APAP product.

Based on the above, it can be readily seen that using acetic anhydride in the purification process affords a superior color-stable product.

EXAMPLES 14–17

Examples 1–13 above are repeated using the same conditions as set forth therein with the exception that the acetylating agent is acetic-propionic anhydride, acetyl chloride, phenyl acetate, and ketene instead of acetic anhydride. The results are substantially the same as those obtained using acetic anhydride and demonstrate, overall, the preparation of a good color-stable product.

It is also within the scope of the present invention to add the acetylating agent at other process steps during the overall purification procedure. However, it is critical that such acetylating agent be added only after the basic reaction is carried out in preparing the APAP, i.e. downstream of the reaction zone. Thus, it falls within the inventive concept to employ the acetylating agent at process points such as (1) crude product filtration, neutralization, and dissolving steps; (2) the carbon treating steps; (3) the filter steps for removing carbon; (4) crystallization steps for precipitating APAP crystal solids; (5) centrifuging steps for removing APAP solids from the mother liquor; and (6) the drying step wherein wet APAP is dried to provide a final product.

Thus, in the scope of the present invention, there is provided a method of preparing N-acetyl-para-aminophenol (APAP) which comprises the steps of reacting acetic anhydride with a mixture of p-aminophenol and water, cooling the reaction mixture to precipitate the APAP, filtering to remove excess acetic acid, neutralizing the wet APAP with a basic material such as ammonium or sodium hydroxide, and agitating the resulting solution with carbon black, wherein the improvement comprises adding substoichiometric quantities of an acetylating agent to the crude APAP at any point after the formation of said crude APAP whereby the color bodies or their precursors in said crude APAP will be substantially converted to non-color bodies (stable, colorless substances); however, substantially none of the APAP is convened to other chemical compounds.

Further, in the scope of the present invention, there is provided a process of preparing an N-acyl-hydroxy aromatic amine which comprises the steps of contacting a hydroxy aromatic ketone with a hydroxylamine salt and a base to form the ketoxime of said ketone, and contacting said ketoxime with a Beckmann rearrangement catalyst to form said crude aromatic amine containing color bodies or their precursors, wherein the improvement comprises the purification of said crude aromatic amine by treating said crude aromatic amine with substoichiometric quantities of an acetylating agent for a sufficient period of time to convert said color bodies or their precursors to substantially non-color bodies (stable, colorless substances); however, substantially none of the APAP is converted to other chemical compounds.

Also, in the scope of the present invention, there is provided a method of preparing N-acetyl-para-aminophenol (APAP) which comprises the steps of reacting 4-hydroxyacetophenone with a hydroxylamine salt and a base to obtain 4-hydroxyacetophenone oxime and then subjecting the 4-hydroxyacetophenone oxime to a Beckmann rearrangement in the presence of a catalyst to form the crude APAP containing color bodies or their precursors wherein the improvement comprises the purification of said crude APAP by treating said crude APAP with substoichiometric quantities of an acetylating agent for a sufficient period of time to convert said color bodies or their precursors to substantially non-color bodies (stable, colorless substances);

however, substantially none of the APAP is converted to other chemical compounds.

It is to be understood, relative to the three (3) processes outlined immediately above, that the term "substantially none of the APAP is converted to other (chemical) compounds" means that less than 400 ppm (parts per million) of 4-AAA is possibly formed by the treatment of the crude APAP with the acetylating agent.

EXAMPLES 18 & 19

Examples 3 and 4 (Runs 3 and 4) above were repeated with the exception that the acetic anhydride was added to the crude APAP solution during the crystallization (cooling) step at two (2) separate temperatures, i.e. 95° C. and 65° C. At the 95° C. level, approximately one third (e.g. 5.2 grams) of the acetic anhydride was added and then at the 65° C. level, the remaining two thirds (e.g. 10.5 grams) was added. The results were substantially the same, with the exception of the 4-AAA content. In repeated Run 3, the 4-AAA content was 40 ppm and in Run 4, it was 41 ppm; this is in comparison to the 207 ppm and 185 ppm 4-AAA content in Examples 3 and 4. This substantial reduction in 4-AAA by the use of a staged addition was quite unexpected.

While the present invention has been described in terms of adding an acetylating agent to an aqueous mixture or solution of APAP, it is within the scope of the present invention to treat a mixture of APAP and an organic solvent with an acetylating agent. Any organic solvent can be utilized as long as it is not reactive with the APAP and acetylating agent. For example, the present invention could be practiced by the addition of substoichiometric quantities of acetic anhydride to crude APAP which is undergoing recrystallization in dioxane; note French patent no. 2672212 which issued Aug. 7, 1992, and which is referred to in Chemical Abstracts 117 (24): 239864f. This reference is incorporated herein in its entirety.

What is claimed is:

1. A method of purifying crude N-acetyl-para-aminophenol (APAP) containing color bodies or their precursors comprising forming a solution of said crude APAP, and subsequently contacting said solution with substoichiometric quantities of an acetylating agent for a sufficient period of time to convert said color bodies or their precursors to substantially stable, colorless substances; said quantities of acetylating agent provided is such that substantially none of the APAP is convened to other compounds.

2. The method of claim 1 wherein said acetylating agent is acetic-propionic anhydride.

3. The method of claim 1 wherein said acetylating agent is acetyl chloride.

4. The method of claim 1 wherein said acetylating agent is phenyl acetate.

5. The method of claim 1 wherein said acetylating agent is ketene.

6. The method of claim 1 wherein said acetylating agent is acetic anhydride.

7. The method of claim 1 wherein said acetylating agent is present in an amount of from about 0.001% to about 2%, based on the weight of the crude APAP.

8. The process of claim 1 wherein the solution of crude APAP is first treated with carbon and the carbon removed prior to contacting said crude APAP with said acetylating agent.

9. In a method of preparing N-acetyl-para-aminophenol (APAP) which comprises the steps of reacting acetic anhydride with a mixture of p-aminophenol and water, cooling the reaction mixture to precipitate crude APAP, filtering to remove excess acetic acid, neutralizing the wet APAP with a basic material, and agitating the resulting solution with carbon black, the improvement which comprises adding substoichiometric quantities of an acetylating agent to the crude APAP at any point after the formation of said crude APAP whereby the color bodies or their precursors in said crude APAP will be substantially converted to stable, colorless substances and substantially none of the APAP is converted to other compounds.

10. In a process of preparing an N-acyl-hydroxy aromatic amine which comprises the steps of contacting a hydroxy aromatic ketone with a hydroxylamine salt and a base to form the ketoxime of said ketone, and contacting said ketoxime with a Beckmann rearrangement catalyst to form a crude N-acyl-hydroxy aromatic amine containing color bodies or their precursors, the improvement which comprises the purification of said crude aromatic amine with substoichiometric quantities of an acetylating agent for a sufficient period of time to convert said color bodies or their precursors to substantially stable, colorless substances and substantially none of the N-acyl-hydroxy aromatic amine is converted to other chemical compounds.

11. In a method of preparing N-acetyl-para-aminophenol (APAP) which comprises the steps of reacting 4-hydroxyacetophenone with a hydroxylamine salt and a base to obtain 4-hydroxyacetophenone oxime and then subjecting the 4-hydroxyacetophenone oxime to a Beckmann rearrangement in the presence of a catalyst to form crude APAP containing color bodies or their precursors, the improvement which comprises the purification of said crude APAP by treating said crude APAP with substoichiometric quantities of an acetylating agent for a sufficient period of time to convert said color bodies or their precursors to substantially stable, colorless substances and substantially none of the APAP is converted to other chemical compounds.

12. The method of claim 11 wherein said acetylating agent is acetic-propionic anhydride.

13. The method of claim 11 wherein said acetylating agent is acetyl chloride.

14. The method of claim 11 wherein said acetylating agent is phenyl acetate.

15. The method of claim 11 wherein said acetylating agent is ketene.

16. The method of claim 11 wherein said acetylating agent is acetic anhydride.

17. The method of claim 11 wherein said acetylating agent is present in an amount of from about 0.001% to about 2%, based on the weight of the crude APAP.

18. The method of claim 11 wherein the crude APAP is first treated with carbon and the carbon removed prior to contacting said crude APAP with said acetylating agent.

19. The method of claim 1 wherein the acetylating agent is contacted with the APAP at one time interval by a single addition thereof.

20. The method of claim 1 wherein the acetylating agent is contacted with the APAP at two different temperature ranges by two different additions thereof.

21. The method of claim 1 wherein there is included a further step which is the crystallization of the APAP in solution by cooling, and the acetylating agent is contacted with the APAP during the crystallization thereof by the continuous addition thereof.

22. The method of claim 20 wherein the contacting is conducted at one temperature range of from about 80° C. to about 110° C. and at a second temperature range of from about 50° C. to about 70° C.

23. The method of claim 1 wherein said acetylating agent is propionic anhydride.

24. The method of claim 1 wherein said solution is an aqueous solution.

25. The method of claim 1 wherein said solution is an organic solvent solution.

* * * * *

UNITED STATES PATENT AND TRADEMARK OFFICE
CERTIFICATE OF CORRECTION

PATENT NO. : 5,399,760
DATED : March 21, 1995
INVENTOR(S) : Edward G. Zey, Olan Stanley Fruchey, Thomas H. Shockley, Joe S. Trevino, B. Frank Wood, Daniel D. Lindley It is certified that error appears in the above-indentified patent and that said Letters Patent is hereby corrected as shown below:

Title page, abstract, line 5, change "quantifies" to "quantities". Column 7, line 50, change "convened" to "converted".

Signed and Sealed this

Twentieth Day of February, 1996

Attest:

BRUCE LEHMAN

*Attesting Officer*     *Commissioner of Patents and Trademarks*